US006850324B1

United States Patent
De Metz

(10) Patent No.: US 6,850,324 B1
(45) Date of Patent: Feb. 1, 2005

(54) DEVICE FOR MEASURING, BY DIFFRACTION, THE SIZES OF SUBSTANTIALLY SPHERICAL PARTICLES, IN PARTICULAR OPAQUE DROPS

(75) Inventor: Jean De Metz, Saint Germain les Corbeil (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/148,354

(22) PCT Filed: Nov. 28, 2000

(86) PCT No.: PCT/FR00/03318

§ 371 (c)(1),
(2), (4) Date: Sep. 4, 2002

(87) PCT Pub. No.: WO01/40766

PCT Pub. Date: Jun. 7, 2001

(30) Foreign Application Priority Data

Nov. 29, 1999 (FR) .............................. 99 14992

(51) Int. Cl.7 ............................................. G01N 15/02
(52) U.S. Cl. ....................................................... 356/336
(58) Field of Search ................................. 356/336–343, 356/432–442; 73/865.5, 865.1; 250/573–575, 222.2

(56) References Cited

U.S. PATENT DOCUMENTS

| 4,037,965 A | | 7/1977 | Weiss |
| 4,341,471 A | * | 7/1982 | Hogg et al. .................. 356/343 |
| 4,735,504 A | | 4/1988 | Tycko |

FOREIGN PATENT DOCUMENTS

| EP | 0864853 | 9/1998 |
| FR | 95.885 | 11/1967 |
| FR | 1.550.406 | 11/1967 |
| GB | 2044445 | 10/1980 |

OTHER PUBLICATIONS

French International Search Report Enclosed.

* cited by examiner

Primary Examiner—Tu T. Nguyen
(74) Attorney, Agent, or Firm—Thelen Reid & Priest LLP

(57) ABSTRACT

A device measures, by diffraction, the sizes of substantially spherical particles, in particular opaque drops. This device includes a lens (46) and prisms (49, 50, 51) for receiving the light diffracted by the particles (12), lighted by a light beam, for splitting this diffracted light into annular concentric areas and for concentrating the various parts of the diffracted light, corresponding to these areas, into separated points (24, 26, 28). The light intensifies in these points are detected and the sizes of particles are determined on the basis of these light intensities. The angular aperture of the concentric areas is adjusted according to a pattern which optimizes the discrimination of particle sizes.

9 Claims, 8 Drawing Sheets

DEVICE FOR MEASURING, BY DIFFRACTION, THE SIZES OF SUBSTANTIALLY SPHERICAL PARTICLES, IN PARTICULAR OPAQUE DROPS

This application is a national phase of PCT/FR00/03318 which was filed on Nov. 28, 2000, and was not published in English.

DESCRIPTION

1. Technical Field

The present invention relates to a device for measuring, by diffraction, the sizes of substantially spherical particles.

It particularly applies to the measurement of the sizes of opaque drops but also has various utilisations in the domain of granulometry.

2. Prior Art

One equipment is commercially available, which carries out the measurement of the size of opaque drop sizes whose diameters range from 0.1 $\mu$m to 10 $\mu$m.

This known equipment illuminates a set of opaque drops using a laser. The drops diffract the light of the laser towards the infinite. For each drop, assumed to be spherical, the diffracted light admits the optical axis of the equipment as a revolution axis.

The diffracted light is measured in the focal plane of a lens. It is known that, in this plane, the lighting E follows the following law:

$$E = E_0 \times N \times \left(\frac{\pi R^2}{\lambda_x F}\right)^2 \times \left(\frac{2J_1(Z)}{Z}\right)^2 \quad (1)$$

where Z is equal to:

$$2\pi \times R \times \frac{\alpha}{\lambda}$$

In this relationship, the illumination E measured in the focal plane relates to N drops proving the same radius R, whose illumination is noted $E_0$ at a wavelength $\lambda$ (for example equal to 0.5 $\mu$m); the focal length F of the lens is 200 mm, for example; a is the diffraction angle and $J_1$ the Bessel function of first order.

To explain the drawbacks of this known device, let us consider two sets of drops, the first one including drops whose diameter is 1 $\mu$m, whereas the second includes 10 $\mu$m diameter drops.

To avoid any cascade diffraction process, The number of drops illuminated by the laser must be limited.

For this purpose, one selects a number N of 1 $\mu$m diameter drops so as to absorb 10% of the light received from the laser. Assuming that the latter ligths a 1 mm² area, the cross section of the N drops set is then 0.1 mm² and the value for N is 127000.

For drops proving the same total mass but whose diameter is 10 $\mu$m, this number is 1000 times lower (i.e 1270 drops) and the light absorption is 1%.

In the focal plane of the device, let's place the end of an optic fibre whose core diameter is equal, to 100 $\mu$m, assuming that the laser delivers a power of 5 watts to illuminate the drops.

On FIG. 1 in the annexed drawings, are presented the variations of the illumination power P (expressed in watts) which is diffracted in the fibre (logarithmic scale), according to the diffraction angle $\alpha$ (expressed in radians), then according to the position of the fibre in the focal plane, for 10 $\mu$m diameter drops (curve I) and for 1 $\mu$m diameter drops (curve II).

The curve III is the "sum" of curves I and II.

One notes that, below 0.06 radians, those drops who have a 10 $\mu$m diameter illuminate the most, whereas the inverse occurs above 0.06 radians.

When the two sets of drops are present and if one limits the measurement within an angular range of 0.06 radians (abscissa of the point A on FIG. 1), one detects only the 10 $\mu$m diameter drops set with an excess of 10% in the number of drops.

With sets proving various drop sizes, the "hollows" of light which appear on FIG. 1 are filled up and the diffracted light power is regularly decreasing when $\alpha$ is increasing.

For 1 mm diameter drops, it must be noted that a more accurate calculation should involve the well-known Mie series.

This known measurement technique, described above, presents the following drawbacks:

The light picked up by the optical fibre, that is the diffracted light intensity, is low, ranging from 15 $\mu$W near the device optical axis to about 50 nW at a diffraction angle of 0.5 radian.

Moreover, the drops are spread at random within the light emitted by the laser.

The interferences between the light fluxes diffracted by each drop induce light peaks.

The respective positions of these peaks, which depend on drop positions, prove no revolution symmetry around the optical axis of the device.

This makes difficult to exploit the measurements aiming at determining drop sizes.

SUMMARY OF THE INVENTION

The purpose of the present invention is to eliminate the above-described drawbacks.

The invention aims at reducing, and even suppressing, the effects of the said light peaks so as to obtain a more reliable determination of the various drop sizes, and, more generally, of the various sizes of particles whose shape is noticeably spherical, in particular particles ranging from 0.1 to 1000 $\mu$m in diameter.

The invention also aims at increasing the quantity of usable diffracted light so as to obtain a more sensitive device, or a device able to work at a faster rate that the above described device.

More precisely, the present invention relates to a device for measuring the sizes of substantially spherical particles, this device being characterised in that it comprises:

a light source able to supply a light beam intended for illuminating the particles, which then diffract the beam light, optical means for concentrating and splitting, intended for receiving the thus diffracted light and able to split this diffracted light into a plurality of concentric annular areas and to concentrate the diffracted light portions, which respectively correspond to these annular areas, into a plurality of points different from each other, and photodetection means intended for detecting the light intensities respectively corresponding to these points, the particle sizes being determined on the basis of these light intensities, device wherein the optical concentrating and splitting means comprise:

optical concentrating means intended for concentrating the diffracted light, the concentrating optical means comprising a focusing optical means with a plane input face and an aspherical output face, and optical splitting means comprising a plurality of annular portions of deviating optical means, these annular portions being intended for intercepting the light thus concentrated, and deflecting the light thus intercepted along directions respectively different from each other.

According to a first particular embodiment of the invention, the said optical deviating means are prisms.

Preferably, the angle of each prism is low, lower than 20°, to avoid geometric aberrations.

According to a second particular embodiment of the invention, the said optical deviating means are light reflecting means.

According to a third particular embodiment of the invention, the said optical deviating means are diffraction gratings.

In the latter case, optical means as described in the following document, herein incorporated by reference, are preferably used:

[1] French patent no 1550406, granted on 12 Nov. 1968 (inventors Jean de Metz and Francois Millet)

or better as described in the following document, herein incorporated by reference:

[2] Addition certificate no 95885 to the French patent no 1550406, granted on 4 Oct. 1971 (inventors Jean de Metz and Francois Millet).

More precisely, according to a first preferred embodiment, the focusing optical means is a lens having a first flat face and a second aspherical face, whose curvature corresponds to a minimum coma, provided, along its axis, with a blind hole opened on the first flat face of the lens, whose wall is polished and whose depth is such that, when a light is sent to the second face, the hole is crossed by the light rays successively reflected by the first face and the second face of the lens.

According to a second preferred embodiment, the focussing optical means is a dioptric system, able to focus at its focus a beam of substantially parallel rays of monochromatic light, interposing only two successive dioptric surfaces on the path of the beam rays, this dioptric system comprising a central lens with a first flat face and a second aspherical face of revolution, whose profile corresponds to a minimum coma, bored along its axis with a through hole with a polished side surface, opening on the first face of the lens, and whose depth is large enough so that, when a light is sent to the second face, the hole is crossed by the light rays successively reflected by the first and second faces of the central lens, and also comprising an annular lens surrounding the central lens, which also has a first flat face and a second aspherical face, protruding from the second face of the central lens along a length such that the light rays successively reflected on the first face and the second face of the annular lens are pseudo-focused outside the lenses.

Preferably, the device according to the invention further comprises means for inhibiting the diffract ion of light at the interfaces of the annular portions included in the concentrating and splitting optical means.

In the present invention, the number of concentric annular areas into which the light diffracted by the particles is split, is preferably equal to M+1, where M is the considered number of different sizes of the particles.

BRIEF DESCRIPTION OF DRAWINGS

The present invention will be better understood when reading the descriptions of examples of embodiments, which do not limit the extent of the invention, referring to the annexed drawings.

DETAILED DESCRIPTION OF PARTICULAR EMBODIMENTS

Figure 2:
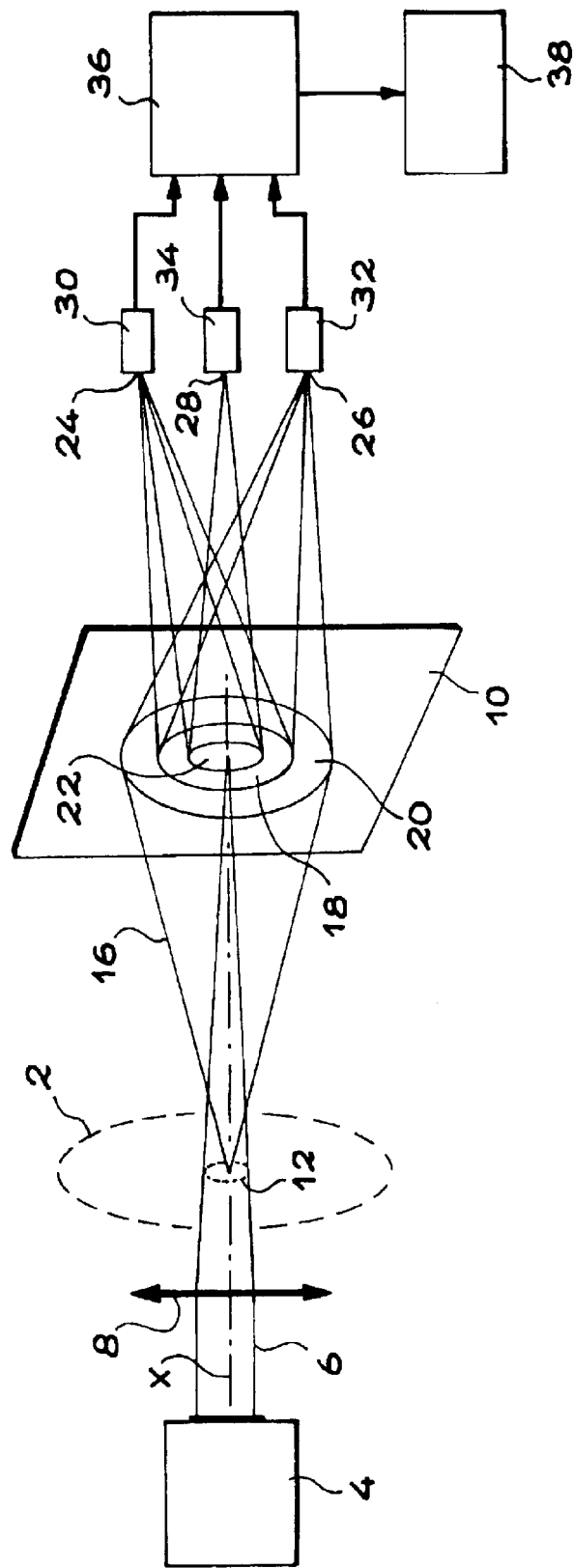
FIG. 2 describes the invention schematically.

The principle of a measuring device following the invention appears on FIG. 2.

This device is intended for measuring the sizes of substantially spherical particles, for example the sizes of opaque drops whose diameters range from 0.1 $\mu$m to 100 $\mu$m. These, for example, may be drops of molten metal, forming a cloud 2, this cloud being produced by means which are not shown.

The device sketched on FIG. 2 comprises a light source 4, for example a laser, which produces a parallel light rays beam 6. This beam is focused by a convergent optical means 8 in a plane 10 which is the focal plane of this optical means 8.

Moreover, as it is shown on FIG. 2, the light beam 6 illuminates a part 12 of the cloud 2 and one intends to measure the sizes of the drops which belong to this part 12 of the cloud and diffract the light of the incident beam 6. More precisely, one intends to measure the number of drops by size in this illuminated part 12.

The light diffracted by the drops in the part 12 is referenced 16 on FIG. 2.

The intersection region of this part 16 with the focal plane 10 (which is perpendicular to the axis X of the beam (6) is split in a plurality of concentric annular areas which present then a symmetry of revolution around an axis perpendicular to the plane 10 (the X axis in the example shown).

In the example shown on FIG. 2, two annular areas 18 and 20 are drawn, as well as the central area 22, the annular area 18 lying between the areas 20 and 22.

One focuses (by focusing means which are not shown) the light of each area onto a point, or more exactly a small spot, so that theses spots are distinct from one another.

In the example of FIG. 2, the spots 24, 26 and 28 thus correspond to the areas 18, 20 and 22.

With this implementation, the sequence of illumination values yielded by areas 18, 20 and 22, which have been located in the plane 10, are no longer submitted to the interference peaks which were hindering the measurement interpretation in the prior art.

Moreover, one collects more light at large incidences, where the light often comes from small drops and proves a lower illumination which overpasses the noise threshold with more difficulty.

FIG. 2 shows also photo-detection means of lights respectively focussed on spots 24, 26 and 28. In the present example, these photo-detection means are photo-detectors 30, 32 and 34, whose number is equal to the number of areas which have been defined in the plane 10.

These photo-detectors supply electrical signals which are representative of the focused light illuminations.

Electronic means 36 are provided for determining, from these signals, the various sizes of the drops which are in the part 12 of the cloud 2.

This determination is achieved, for example, via the method described in the following document:

B. Arad, New method for studying debris from laser induced spall in metals, Review of Scientific Instruments, vol. 66, no 12, December 1995, p. 5590 to 5597.

The processing means 36 are provided with display means 38 which are shown on FIG. 2.

FIG. 3–6 are schematic cross-sections of various concentrating and splitting optical means which are intended for receiving the diffracted light 16, splitting this light into concentric annular areas and concentrating the parts of the diffracted light which respectively correspond to these annular areas, at points or focuses 24, 26, 28 which are distinct from one another.

Figure 3:
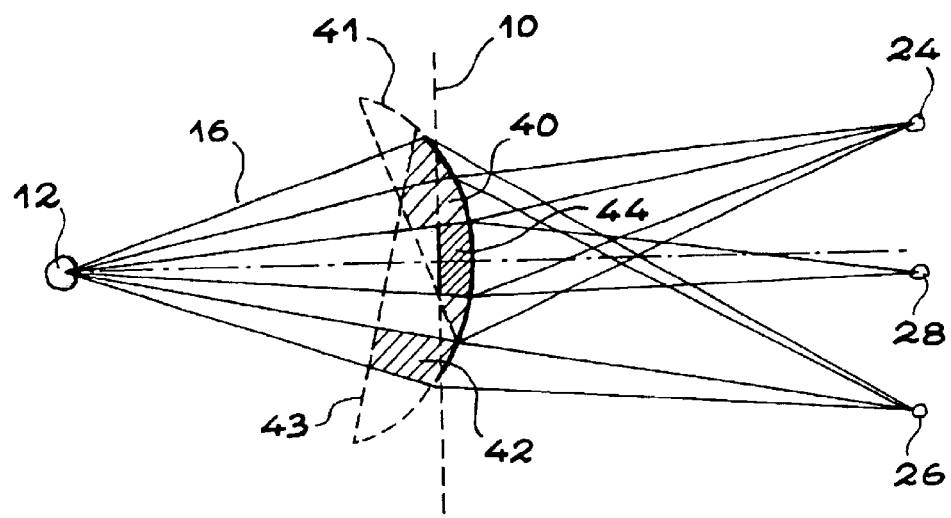
FIG. 3 is a partial schematic cross-section of a device, described for a good understanding of the invention, using annular portions of convergent lenses.
Figure 4:
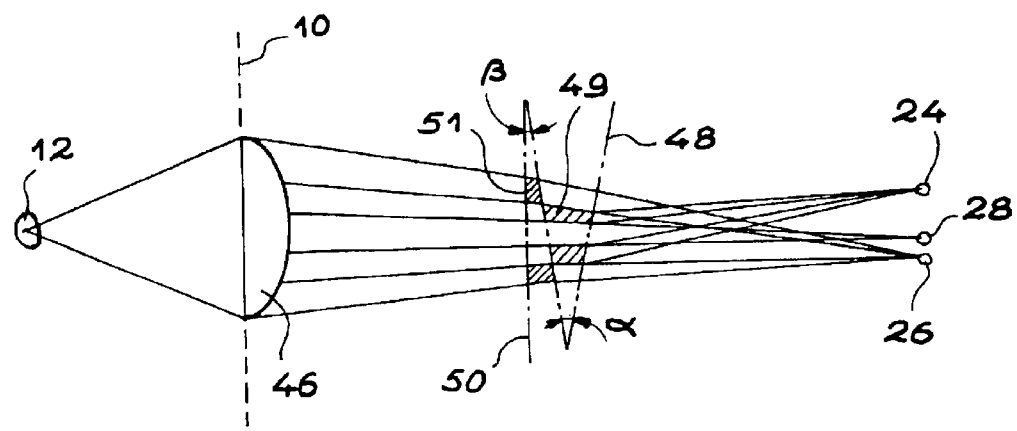
FIG. 4A is a partial and schematic cross-section view of a device according to the invention, using annular portions of prisms.
FIGS. 4B and 4C schematically describe examples of focusing optical means liable to be used in the invention.
Figure 4:
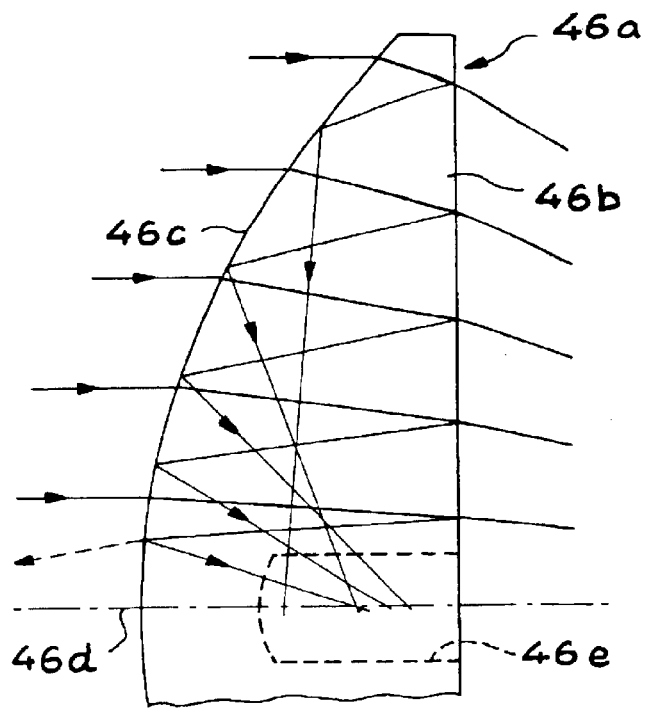
Figure 4:
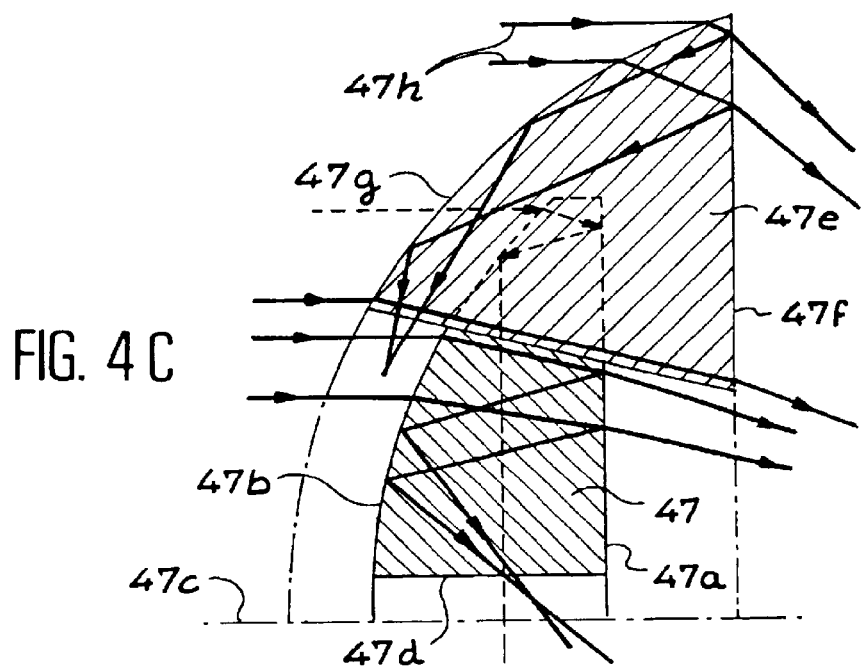

The example shown of FIG. 3, useful for a good understanding of the invention, features concurrently achieved concentrating and splitting processes. As it can be seen on this FIG. 3, one uses a glass ring 40 which is cut out from a convergent lens 41, drawn as a dotted curve, which focuses the light at its focus 24.

Another glass ring 42 is used, which is cut out from another convergent lens 43, drawn as a dotted line, which focuses the light at its focus 26.

The cross section of the ring 42 is off-axis so that the focus 26 is different from the focus 24 as seen on FIG. 3.

The glass ring set 40, 42 is completed by a central portion of the lens 44, whose focus 28 is distinct from focuses 24 and 26.

The set comprising the rings 40, 42 and the portion of the lens 44 is located substantially close to the focal plane 10.

For example, a set of 50 rings plus the centre part of the lens 44 can be created. This set can be reproduced via a moulding process.

The example of FIG. 4A features separate concentrating and splitting functions, obtained by using specific components.

The concentrating function is obtained by using a convergent optical means 46 substantially located at the focal plane 10.

Preferably, the optical means is a planar-aspherical glass lens, whose refraction index is equal to 1.618, as described in the above-mentioned document [1].

It must be pointed out, referring to FIG. 4B, that the said means is a single lens 46a whose output face 46b is flat, whereas its input face 46c is aspherical, with a curvature providing for a minimum coma, bored along its axis 46d with a blind hole 46a whose opening is on the output face of the lens, whose peripheral surface is polished and whose depth is such that it is traversed by the light rays successively reflected by the output face and the input face of the lens.

Another embodiment may involve optical means such as described in the above-cited document [2].

Referring to FIG. 4C, it is noteworthy that this device is a dioptric system intended to focus at its focus a monochromatic beam of light, made of noticeably parallel rays, involving two successive dioptric surfaces only on the path of the light rays which constitute the beam. This dioptric system comprises a central lens 47 whose output face 47a is flat and input face 47b is an aspherical face of revolution, whose profile corresponds to a minimum coma, and which is provided with a hole 47d along its axis 47c opened on the output face of the lens, with a polished internal side, deep enough to be traversed by the light rays successively reflected by the output and input faces of the central lens, and an annular lens 47e surrounding the central lens, featuring also a flat output face 47f and an aspherical input face 47g, protruding from the front face of the central lens over a length such that the rays 47h successively reflected by the output and the input faces of the annular lens are pseudo-focussed outside the lenses.

In the present invention, the two optical means described in the above-cited documents are inverted: the flat faces of lenses are used as input faces for the beam diffracted by the particles and the aspherical faces as output faces so as to obtain a substantially parallel output beam.

Such an optical means yields a minimum of geometric aberrations for an image of small size.

In the example of FIG. 4A, the splitting function is achieved via a set of prisms, namely two prisms 48 and 50 in the shown example, assuming that, for each prism, only a ring-shaped portion is kept.

The prisms 48 and 50 are drawn in dotted lines and the rings respectively corresponding to prisms 48 and 50 are referenced 49 and 51.

It must be noted that the orientations of prisms are different so as to obtain separate focuses 24, 26 and 28.

Moreover, the angles of the said prisms prove a low value, lower than 20° to avoid aberrations. In this example, the angles $\alpha$ and $\beta$ of prisms 48 and 50 respectively have values of 10° and 5°.

On FIG. 4A, the prisms are presented as adjoining but the rings, once realised, are made fit into one another.

The selected dimensions of prisms depend on the distance between the set of portions 49 and 51 and the optical system 46, to obtain an accurate coverage of the angular areas of interest.

Figure 5:
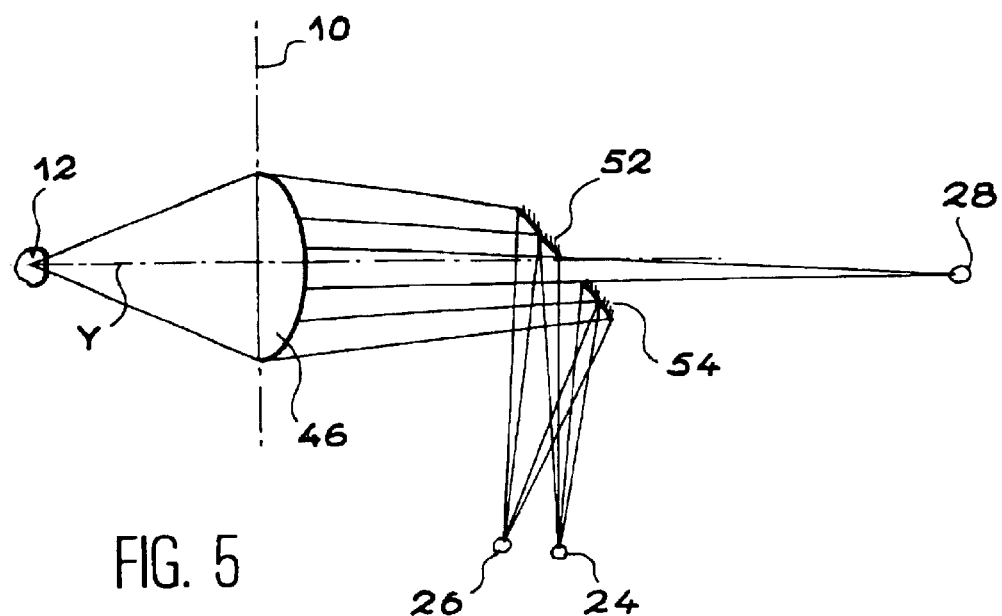
FIG. 5 is a schematic and partial cross-section view of another device according to the invention, using annular portions of mirrors.

In the example of FIG. 5, the splitting function is obtained via a set of annular mirrors, namely two annular mirrors 52 and 54 in the presented example.

The central hole of the mirrors set lets a part of light pass through, the latter being focused by the optical system 46 at spot 28.

The annular mirrors 52 and 54 deviate parts of light which are focused at points 24 and 26.

It must be pointed out that the annular mirrors present different inclinations with respect to the axis Y of the optical system 46 and are bored with elliptical holes so that the light delivered by this optical system 46 is spread into circular areas.

Figure 6:
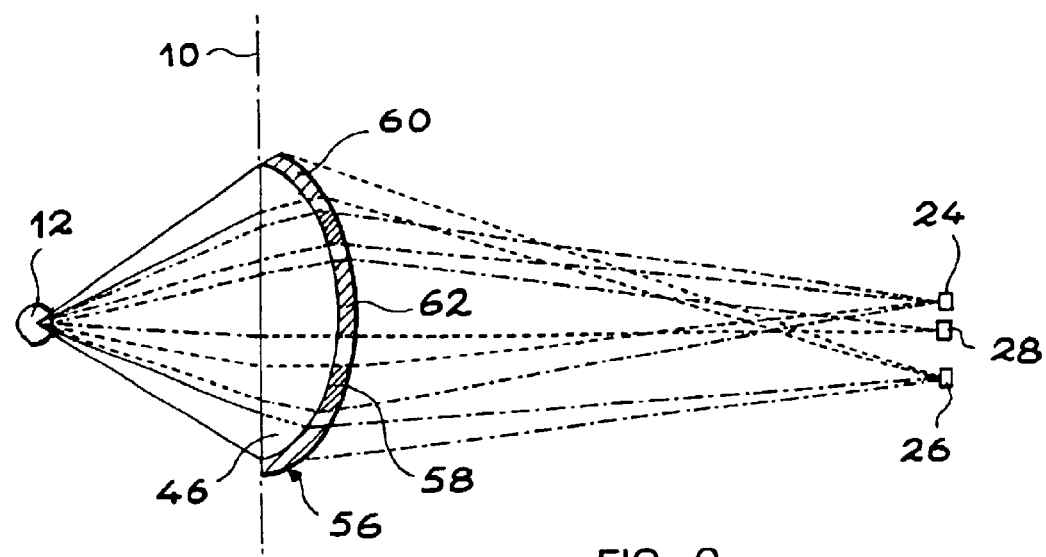
FIG. 6 is a schematic and partial cross-section view of another device according to the invention, using annular portions of diffraction gratings.

In the example of FIG. 6, the splitting function is achieved via a photoresist layer 56 deposited on the convex surface of the optical system 46 wherein annular concentric gratings are created, namely two diffraction gratings 58 and 60 in the presented example, as well as a central diffraction grating 62 as shown on FIG. 6.

These gratings 58, 60 and 62 are holograms intended for deviating light supplied by the optical system 46 respectively towards spots 24, 26 and 28.

For creating the gratings 58, 60 and 62, one successively insolates the areas of the photoresist which corresponds to these gratings so as to obtain the holograms.

For each insolation, one uses two laser sources which are formed
in the area 12 and at point 24 to obtain the grating 58,
in the area 12 and at point 26 to obtain the grating 60,
in the area 12 and at point 28 to obtain the grating 62,
and which, in each of these three cases, create interferences within the adequate area of the photoresist for forming the corresponding hologram therein.

The thickness of the photoresist is correctly adjusted so as to obtain only one order of interference in each case.

The insolation of each area of the photoresist 56 is made through two adequate masks which prevent the insolation of the rest of this layer 56 by each of the two laser source.

Figure 7:
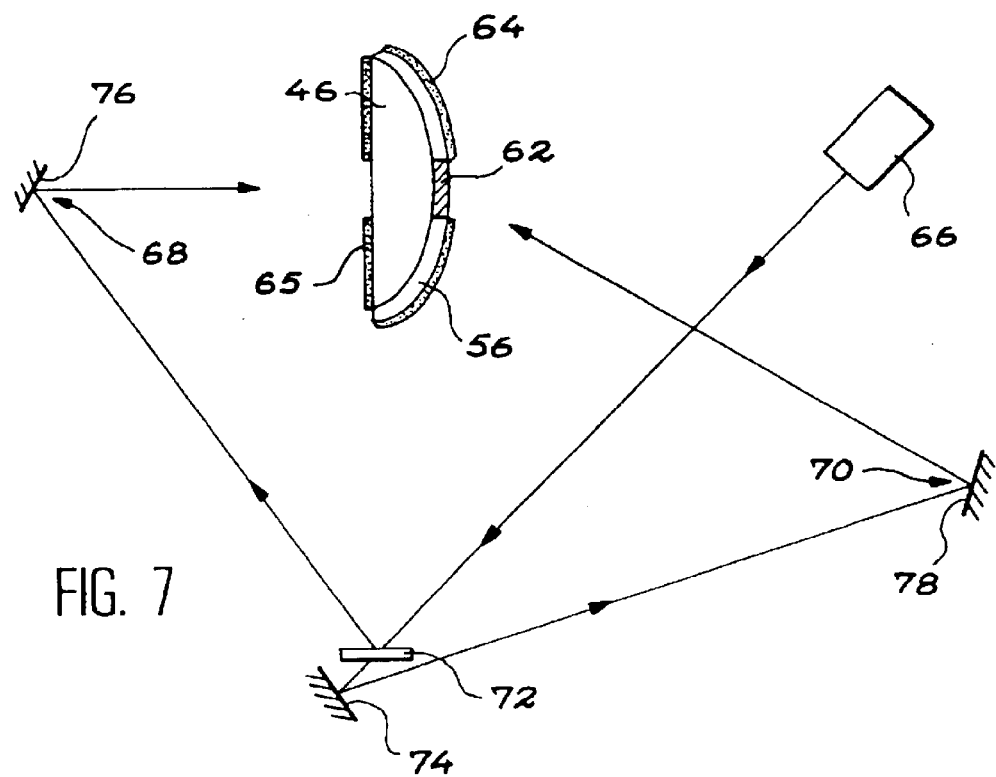
FIG. 7 is a schematics of the realisation of theses annular portions of diffraction gratings.

FIG. 7 gives a sketch, as an example, of the insolation of the layer 56 onto which the central diffraction grating 62 is to be formed.

Two masks 64 and 65 prevent the insolation of the rest of the layer 56 by beams supplied by the laser sources 68 and 70 which appear on FIG. 7.

One laser 66 only is used to obtain the laser source 68 within the part of the drops cloud 12 and the other laser source 70 at the focus or spot 28.

For that purpose, a semi-reflecting mirror 72 and laser reflectors 74, 76 and 78 are arranged adequately as is shown on FIG. 7, as it is current practice in the domain of holography.

After developing the insulated layer 56, three holographic gratings are obtained, which focus light at points 24, 26 and 28.

According to another particular embodiment (not shown), the photoresist layer is spread onto the flat plane of the optical system 46. In this case, the insolation process yield a supplementary correction of aberrations, already reduced by the use of an optical combination of the kind described in document [1] or document [2] and permits to obtain a good image of the part 12 of the drops cloud on each of photodetectors which are located at points 24, 26 and 28 as seen above.

According to another particular embodiment (not shown), the photoresist layer is not spread onto the optical system 46 but on a glass blade at a distance of this optical system 46, the photoresist being located between the glass blade and the part 12 under study of the drops cloud.

For each of the arrangements which are described schematically and partially on FIG. 3 to 6, it must be made clear that, for evaluating the measurements allowing to know the various drop sizes, one must calibrate the device regarding the illumination yielded by each ring, checking that each ring illuminates one photodetector only.

For computerising measurements, it is advisable to use a photodetectors array, for example a photodiode strip or a CCD-type (coupled charge detector) detector.

In the latter case, the concentrating and splitting means are organised so that the various spots where the light is concentrated (referenced 24, 26 and 28 on FIGS. 3 to 6) are located so as to allow the use of the said detecting devices.

If, for example, a photodiode strip is used, the said spots must be lined up.

Let's come back to the device described on FIG. 3.

Preferably, to get only "useful" light at the output of the set of rings 40, 42 and 44, and discard any parasitic light which should be liable to be diffracted at the edges as well as on the internal and external surfaces of each ring, it is necessary to avoid that the diffracted light "touches" these parts.

For this purpose, the external and internal edges are chamfered on the side of the incoming light, and each chamfer is made opaque using black paint.

Figure 8:
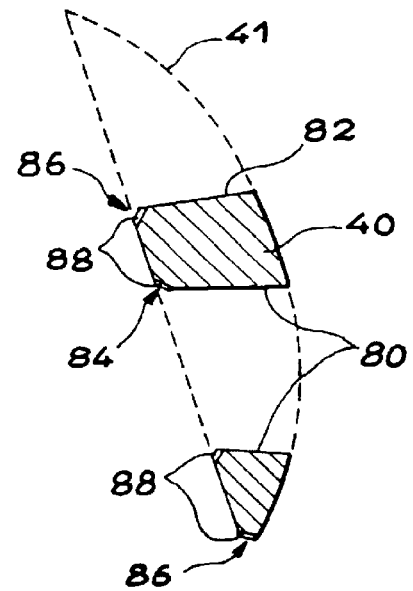
FIG. 8 schematically illustrates the possibility of forming chamfers on the annular portions of lenses shown on FIG. 3, for improving the operation of the corresponding measuring device

This is sketched on FIG. 8, taking the ring 40 of FIG. 3 as an example.

FIG. 8 shows the internal edge 80 and the external edge 82 of the said ring 40. One also sees the chamfers 84 and 86 respectively machined on the edges 80 and 82 as well as the black paint layer coating each chamfer.

Preferably, the same process is applied in the case when annular portions of prisms are used (FIG. 4A).

The same way, when the diffraction gratings of FIG. 6 are used, light absorbing areas are preferably created between the insolated areas. For this purpose, a black paint ring is deposited where required.

Let us now deal with the determination of the rings angular limits.

It has been shown (FIG. 1), that the light was coming at small angles from large drops and at large angles from small drops.

Figure 1:
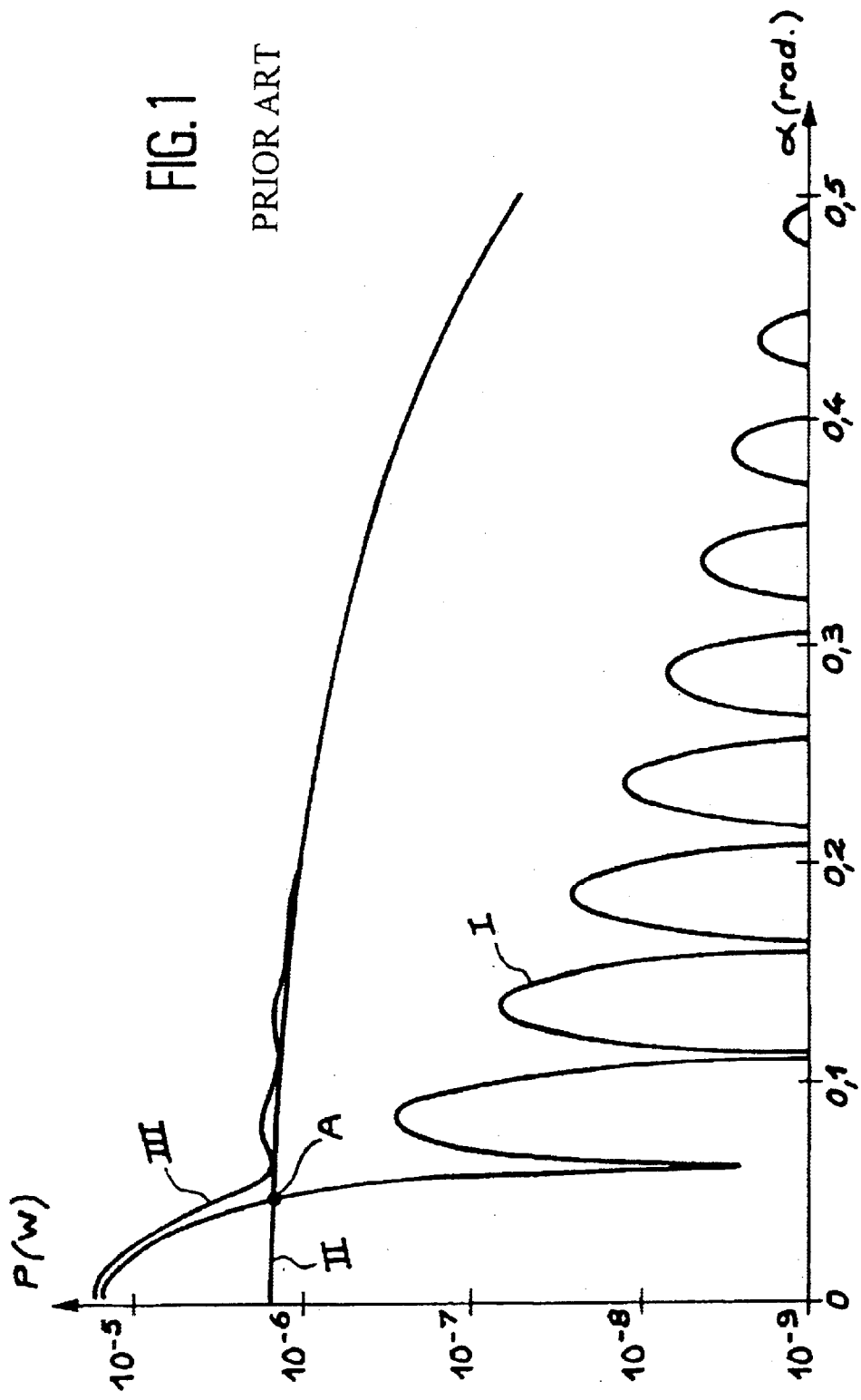
FIG. 1 represents the power variations of the light diffracted by the drops in a fibre in terms of the diffraction angle, for two drops sizes it has been described above.
Figure 9:
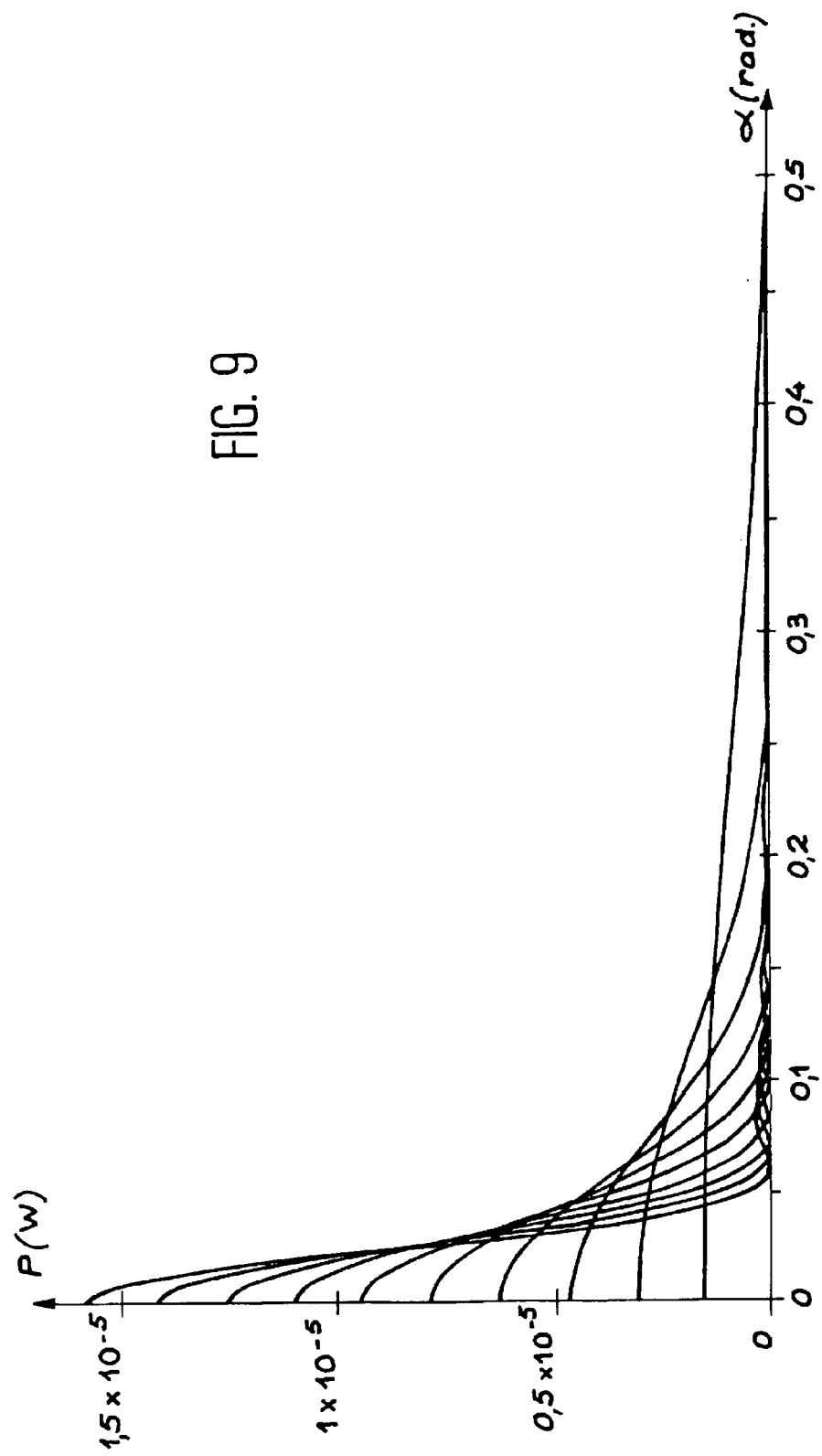
FIGS. 9 and 10 show curves for explaining the determination of the angular limitations of rings used in the invention.

One can plot, using the relation (1) stated above, a series of curves (FIG. 9) corresponding to ten sizes from 1 $\mu$m to 10 $\mu$m, by steps of 1 $\mu$m, instead of the two curves I and II of FIG. 1.

Figure 10:
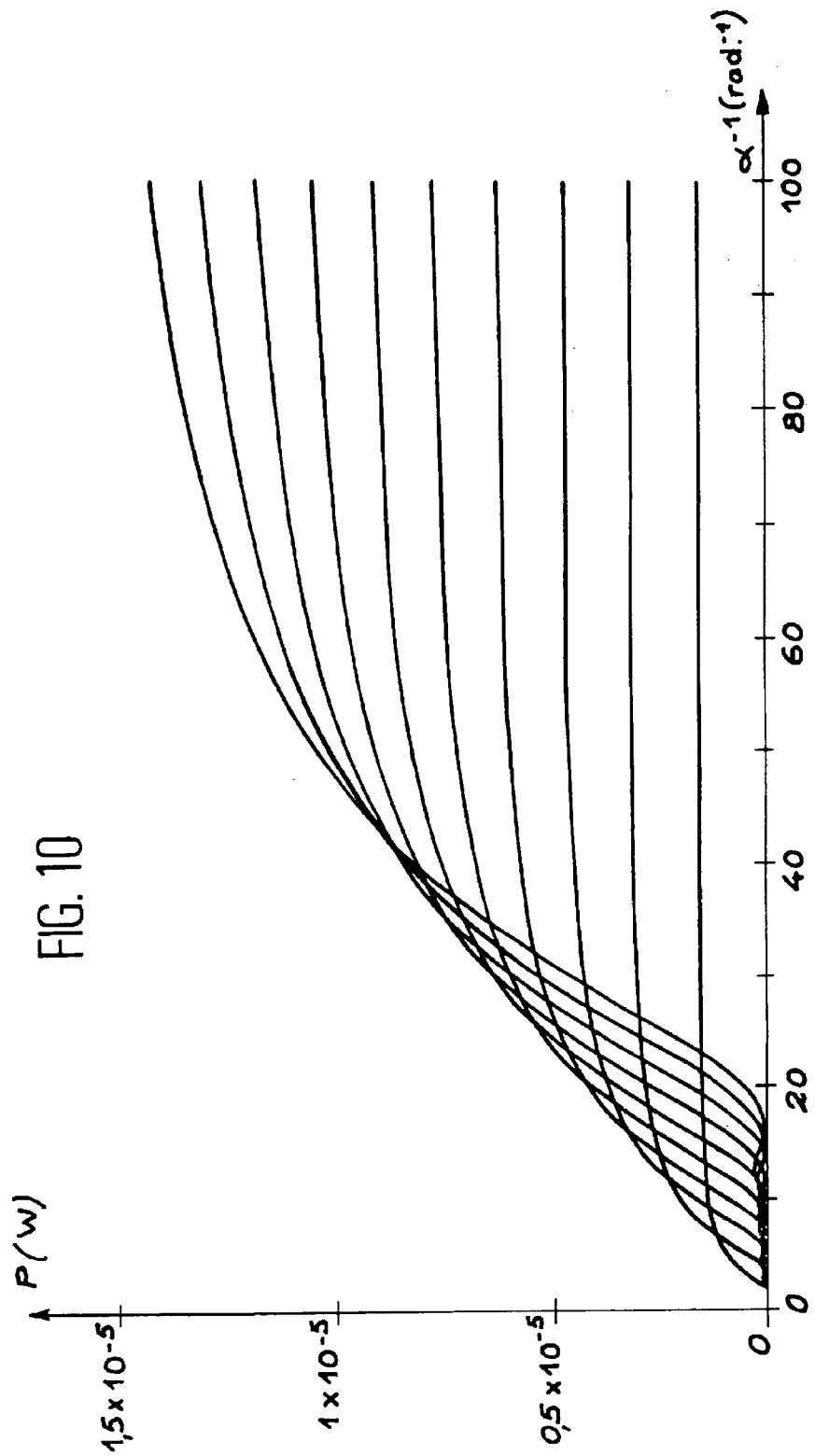

Since the envelope of these curves looks like an hyperbole, one plots on FIG. 10 the same series of curves, placing in abscissa the inverse values $\alpha^{-1}$ (expressed in radiansr$^{-1}$) of angles $\alpha$. The envelope then becomes a straight line segment which corresponds to a value of Z near to 1.36, where $Z=2\pi R x \alpha/\lambda$ is hereinabove defined.

It can be seen that each size of drop yields the maximum illumination within a particular angular interval. This interval is defined by the value and the expression of Z as stated by relation (1).

To get the best illumination for a given size of drop, one must then place a ring in the focal plane 10. It is the location where one obtains the best discrimination.

A law is thus derived for defining discrimination regions in the focal plane.

The following table I, for example, gives an assembly of 11 rings, intended for receiving the light from particles whose size ranges from 0.84 $\mu$m to 9 $\mu$m, for a diffracted light having a wavelength of 0.5 $\mu$m. The optimal ring cutting is performed according to the law:

$$1.36=2\pi R\ (\alpha/\lambda).$$

This law optimises the drop size discrimination.

TABLE I

| Ring Number | Ring cut from angle | to angle | Best seen diameter |
|---|---|---|---|
| 1 | 26° | 9.8° | 0.84 $\mu$m |
| 2 | 9.8° | 6° | 1.66 $\mu$m |
| 3 | 6° | 4.3° | 2.5 $\mu$m |
| 4 | 4.3° | 3.3° | 3.3 $\mu$m |

TABLE I-continued

| Ring | Ring cut | | Best seen |
| --- | --- | --- | --- |
| Number | from angle | to angle | diameter |
| 5 | 3.3° | 2.7° | 4.1 µm |
| 6 | 2.7° | 2.3° | 5 µm |
| 7 | 2.3° | 2.0° | 5.8 µm |
| 8 | 2.0° | 1.77° | 6.6 µm |
| 9 | 1.77° | 1.58° | 7.4 µm |
| 10 | 1.58° | 1.43° | 8.2 µm |
| 11 | 1.43° | 1.30° | 9 µm |

Let us now examine how to fix the preferred number of rings.

FIG. 1 also shows that one measurement alone of the illumination E, e.g. carried out at α=0.06 radian, does not permit to know if the drop family has a diameter of 1 µm or 10 µm nor to know the number of points. Using the measurement of the illumination $E_0$ of drops, two solutions would be obtained for this number: 127000 1 µm diameter drops or 1270 10µm diameter drops.

A measurement of the opacity showing an absorption of 1% would prove that the diffracting family is formed of 10 µm drops. One second measurement at another angle would have confirmed that.

Generally speaking, one needs M+1 measurements (angles, opacity, drop illumination) to obtain the number of diffracting drops of each size among M sizes.

M+1 rings are therefore used preferably.

This number must not be increased too much, as each ring, in a device according to the invention, collects a fraction only, equal to 1/M, of all the light received by the concentrating and splitting means of such a device.

In the invention, all the diffracted light is collected at the optimum angles which correspond to the sizes searched for. This eliminates the effect of interference peaks, which was hindering the evaluation of measurements in the prior art. This also provides for the maximum of sensitiveness used either for measuring lower concentrations of particles or for maximising the fastness of data acquisition.

The present invention is not limited to the measurement of the size of opaque drops whose diameters range from 0.1 µm to 100 µm.

It applies also to the measurement of sizes of all kinds of particles whose shape is substantially spherical, these particles being transparent or translucent or opaque and proving sizes which range from 0.1 µm to 1 mm.

The invention, for example, may be used for the granulometry of powders of materials such as plaster, cement and iron ore.

Then one illuminates a powder of this kind, placed in front of a device according the invention, on a plate which is transparent to the used light and which is maintained fixed or moving in front of the device.

Devices, for measuring the energy and direction of a light flux coming from particles, in order to determine the characteristics of these particles are known from the document GB 2044445A (Coulter Electronics). These devices mainly comprise focusing-splitting means which involve non flat mirrors, in which the focusing means are not separate from the splitting means.

Such devices do not permit a correct measurement of the size of particles, except when the said particles are exactly located at the focus of mirrors. For other particles, the geometric aberrations of mirrors forbid correct measurements.

The present invention overcomes this drawback thanks to the use of concentrating optical means, comprising a focusing optical means with a flat input face and an aspheric output face, and optical splitting means distinct from the concentrating optical means. A good image is then obtained, over an optical field of about 1°.

What is claimed is:

1. A device for measuring the sizes of substantially spherical particles comprising:

a light source supplying a light beam for illuminating the particles, which then diffract the light beam;

optical means for splitting the diffracted light beam into a plurality of concentric annular areas;

optical means for concentrating the diffracted light beam, which respectively correspond to said plurality of concentric annular areas, into a plurality of points different from each other; and photodetection means for detecting the light intensities respectively corresponding to these points, the particle sizes being determined on the basis of these light intensities, wherein the optical means for concentrating comprise a focusing optical means having a plane input face and an aspherical output face, and wherein the optical means for splitting comprise a plurality of annular portions of deviating optical means, these annular portions intercepting the concentrated light, and deflecting the light intercepted along their respective directions which are different from each other.

2. Device according to claim 1, wherein the deviating optical means are prisms (48,50).

3. Device according to claim 2, wherein the angle (a, β) of each prism is lower than 20°.

4. Device according to claim 1, wherein the deviating optical means are light reflecting means.

5. Device according to claim 1, wherein the deviating optical means are diffraction gratings.

6. Device according to claim 1, further comprising means for inhibiting the diffraction of light at the interfaces of the annular portions included in the splitting optical means.

7. Device according to claim 1, wherein the number of concentric annular areas is equal to M+1, where M is the considered number of different sizes of particles.

8. Device according to claim 1, wherein the focusing optical means is a lens having a first flat face and a second aspherical face, whose curvature corresponds to a minimum coma, provided, along its axis, with a blind hole opened on the first flat face of the lens, whose wall is polished and whose depth is such that, when a light is sent to the second face, the hole is crossed by the light rays successively reflected by the first face and the second face of the lens.

9. Device according to claim 1, wherein the focusing optical means is a dioptric system, able to focus at its focus a beam of substantially parallel rays of monochromatic light, interposing only two successive dioptric surfaces on the path of the beam rays, this dioptric system comprising a central lens with a first flat face and a second aspherical face of revolution, whose profile corresponds to a minimum coma, bored along its axis with a through hole with a polished side surface, opening on the first face of the lens, and whose depth is large enough so that, when a light is sent to the second face, the hole is crossed by the light rays successively reflected by the first and second faces of the central lens, and also comprising an annular lens surrounding the central lens, which also has a first flat face and a second aspherical face, protruding from the second face of the central lens along a length such that the light rays successively reflected on the first face and the second face of the annular lens are pseudo-focused outside the lenses.

* * * * *